United States Patent [19]

Blum

[11] Patent Number: 4,931,442

[45] Date of Patent: Jun. 5, 1990

[54] STABILIZED AQUEOUS FOLIC ACID PREPARATION

[76] Inventor: Holger Blum, Parkallee 75, D-2000 Hamburg 13, Fed. Rep. of Germany

[21] Appl. No.: 280,351

[22] Filed: Dec. 6, 1988

[30] Foreign Application Priority Data

Dec. 7, 1987 [EP] European Pat. Off. ........ 87118082.4

[51] Int. Cl.$^5$ ............................................ A61K 31/505
[52] U.S. Cl. .................... 514/249; 544/258; 544/261
[58] Field of Search ................. 544/261, 258; 514/249

[56] References Cited

U.S. PATENT DOCUMENTS

| | | | |
|---|---|---|---|
| 2,695,860 | 11/1954 | Weidenheimer | 514/249 |
| 2,731,390 | 1/1956 | Tansey et al. | 514/249 |
| 2,927,113 | 3/1960 | D'Amato | 544/258 |
| 3,914,419 | 10/1985 | Haeger et al. | 514/249 |
| 4,350,659 | 9/1982 | Riceberg | 544/261 |
| 4,804,535 | 2/1989 | Kesselman | 514/249 |

FOREIGN PATENT DOCUMENTS 0175432  10/1984  Japan ................... 544/258

OTHER PUBLICATIONS

Koft et al, Jour. Am. Chem. Soc., vol. 71, p. 3245, (1949).
Tripet et al, Pharm. Acta. Helv., vol. 50, pp. 318–322, (1975).
Horwiz, ed., "Official Methods of Analysis of the Ass'n of Official Analytical Chemists", 13 ed. 1980, Wash., D.C., (1980), pp. 759–763, Beilstein E. III/IV, p. 3934.

*Primary Examiner*—Donald G. Daus
*Attorney, Agent, or Firm*—Fleit, Jacobson, Cohn, Price, Holman & Stern

[57] ABSTRACT

This invention relates to a stabilized aqueous folic acid preparation which comprises a folic acid component selected from the group consisting of folic acid, ammonium, alkali metal and alkaline earth metal salts of folic acid and mixtures thereof, and which has an improved stability of its folic acid contents in the presence of oxygen, the said preparation containing as a stabilizer a combination of (a) at least one member selected from the group consisting of dihydrofolic acid and ammonium, alkali metal, alkaline earth metal and alkanolammonium salts thereof, and (b) at least one member selected from the group consisting of at least one hydroxypolycarboxylic acid and ammonium, alkali metal, alkaline earth metal and alkanolammonium salts thereof.

5 Claims, No Drawings

STABILIZED AQUEOUS FOLIC ACID PREPARATION

FIELD OF THE INVENTION

This invention relates to stabilized aqueous folic acid preparations and more specifically to aqueous vitamine preparations containing at least one member of the group selected from folic acid (also known as pteroylglutamic acid) and ammonium, alkali metal and alkaline earth metal salts thereof, which have an improved stability of the folic acid contents in the presence of oxygen.

BACKGROUND OF THE INVENTION

Aqueous solutions of folic acid or salts thereof have only a limited stability in the presence of oxygen. In the presence of buffered solutions, the folic acid molecule is cleaved within a more or less short period of time into biologically inactive fragments, too (cf. B. Koft, G. Sevag in J. Am. Chem. Soc. 71, 3245 (1949)). For initiation of this decomposition of the folic acid a high humidity of the air is already sufficient (cf. F. Y. Triptet, U. W. Kesselring in Pharm. Acta Helv. 50 (10), 318–322 (1975)).

From British Pat. No. 725,683 it is known that aqueous solutions of alkali metal salts of folic acid may be stabilized by the addition of alkali metal salts of ethylenediaminetetraacetic acid. However, in practice it has turned out that the addition of the alkali metal salts of ethylenediaminetetraacetic acid has only a low stabilizing effect against oxygen contained in the air. Further, the use of ethylenediaminetetraacetic acid is physiologically problematic, when the vitamine preparation is to be used for the feeding of animals or for related application fields.

In cases where aqueous folic acid solutions have to be stored in the presence of air for extended periods of time, e.g. for several weeks, as is the case, for example, when they are used in biological sewage treatment plants, a significant decrease in bioactivity of the aqueous folic acid solutions had to be put up with, when using previous methods of stabilization.

It is the problem underlying the present invention to show a way to impart storage stability to aqueous solutions of folic acid and/or of salts thereof in the presence of oxygen, i.e. to impart a longer lasting stability to them.

SUMMARY OF THE INVENTION

This invention provides a stabilized aqueous folic acid preparation which comprises a folic acid component selected from the group consisting of folic acid, ammonium, alkali metal and alkaline earth metal salts of folic acid and mixtures thereof, and which has an improved stability of its folic acid contents in the presence of oxygen, the said preparation containing as a stabilizer a combination of (a) at least one member selected from the group consisting of dihydrofolic acid and ammonium, alkali metal, alkaline earth metal and alkanolammonium salts thereof, and (b) at least one member selected from the group consisting of at least one hydroxypolycarboxylic acid and ammonium, alkali metal, alkaline earth metal and alkanolammonium salts thereof.

DETAILED DISCLOSURE OF THE INVENTION

The aqueous folic acid solutions of the invention, specifically the aqueous vitamine preparations containing folic acid and/or at least one ammonium, alkali metal and alkaline earth metal salts thereof, can be stored in the presence of oxygen for extended periods of time, e.g. several weeks, without occurance of a substantial decrease in bioactivity. They have an excellent storage stability which goes back to the synergistic activity of the stabilizer combination used according to the invention, which could not be achieved with stabilizers previously known.

According to a preferred embodiment of the invention the aqueous preparations contain dihydrofolic acid and/or at least one ammonium, alkali metal, alkaline earth metal or alkanolammonium salt thereof in an amount of 0.001 to 0.1 mol, preferably in an amount of 0.01 to 0.1 mol, and the hydroxypolycarboxylic acid in an amount of 0.05 to 2.5 mol, per mol of folic acid and/or folic acid salts to be stabilized.

Preferably the hydroxypolycarboxylic acid to be used according to the invention is citric acid, tartaric acid or malic acid.

The alkanolammonium salt preferably is a salt of the above mentioned organic acids with a dialkanolamine of the formula

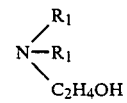

wherein each $R_1$ independently is hydrogen, hydroxyethyl or hydroxypropyl.

The folic acid to be stabilized according to the invention, which is also known as pteroylglutamic acid, is a vitamine of the B-group. It has the formula

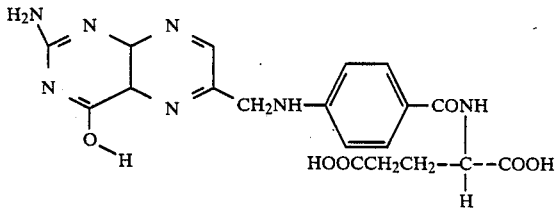

The above mentioned alkali metal salts are the lithium, sodium, potassium, rubidium and caesium salts.

The above mentioned term "ammonium salts" comprises both the ammonium salts and the tetraalkyl ammonium salts represented by $NH_4^+$ and $NR_4^+$, respectively, wherein R is a lower alkyl residue, which preferably has 1 to 6, more preferably 1 to 4, and most preferably 1 to 3 carbon atoms.

The term "alkaline earth metal salts", as used throughout the specification, means the magnesium, calcium, strontium and barium salts.

The dihydrofolic acid to be used according to the invention is a substance sensitive to oxidation, which decomposes in aqueous solution in the presence of oxygen into amino benzoyl glutamic acid and pteric acid. Therefore, the finding was quite surprising, that a substance, which itself is sensitive to oxidation, is capable of inhibiting the oxidative decomposition of folic acid in aqueous solution.

The preparation of dihydrofolic acid of the formula given below

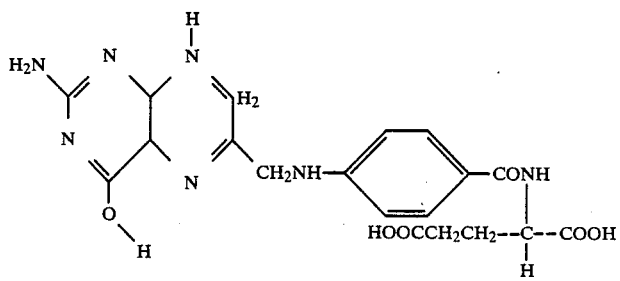

is carried out in a way known per se by partial reduction of folic acid, for example according to S. Futtermann, J. Biol. Chem. 228, 1031 (1957).

A particular advantage of the aqueous preparations of the invention is that in contrast to known stabilizers previously used for aqueous folic acid solutions, the dihydrofolic acid to be used as stabilizer is no foreign material for cells, but is formed from a number of enzymes from folic acid as a precursor for, e.g., the growth factor citrovorum (cf. E. Beilstein, III/IV, page 3934).

In order to achieve a sufficient storage stability of the aqueous folic acid solutions, generally 0.001 to 0.1 mols, preferably 0.01 to 0.1 mols, of dihydrofolic acid per mol folic acid have to be added to the folic acid to be stabilized. Particularly small amounts of dihydrofolic acid may be used, when a second stabilizer in the form of a hydroxypolycarboxylic acid is used in the aqueous vitamine preparation besides dihydrofolic acid. Examples for suitable hydroxypolycarboxylic acids are tartaric acid, citric acid and malic acid.

The activity of the individual stabilizers for the storage of aqueous folic acid solutions is evaluated by drawing samples at the beginning and at the end of the storage period and microbiologically determining their folic acid contents. In case the amounts of the sample drawn from the vitamine preparation are equally large, the stability is easily determined by calculating the quotient:

$$\text{STABILITY} = 100 \times \frac{\text{(folic acid contents at the end of the storage period)}}{\text{(folic acid contents an the beginning of the storage period)}} \quad (1)$$

Methods for microbiologically determining the folic acid contents are known to the one skilled in the art. A suitable description is to be found in "Official Methods of Analysis of the Association of Official Analytical Chemists", Washington, DC 20044, 13th edition 1980, AOAC Methods (1980), 759–763.

The following examples are to illustrate the present invention, however, it is to be understood that the invention is not limited thereto.

EXAMPLES 1 TO 8

In order to illustrate the stabilizing activity of dihydrofolic acid in its synergistic combination with hydroxypolycarboxylic acids, several aqueous vitamine preparations were prepared, which had the composition given below.

100 g each of the so prepared vitamine preparations were stored in an open brown glass bottle of 280 ml contents at room temperature for the period of time given in table I below. At the end of this storage period the measured evaporation losses were refilled with water and the folic acid contents was determined microbiologically according to the AOAC methods. The stability was calculated according to the formula (1) given above.

Preparation A

An aqueous solution of folic acid, dihydrofolic acid and citric acid was prepared using sodium hydroxide solution. The pH value of the solution was 10.4. 100 g solution contained 16 mmol folic acid disodium salt, 1 mmol dihydrofolic acid, sodium salt, and 5 mmol trisodium citrate.

Preparation B

An aqueous solution of folic acid and dihydrofolic acid was prepared using sodium hydroxide solution. The pH value of the solution was 10.2. 100 g solution contained 16 mmol folic acid, disodium salt, and 4 mmol dihydrofolic acid, sodium salt.

Preparation C

An aqueous solution of folic acid, dihydrofolic acid and citric acid was prepared using sodium hydroxide solution. The pH value of the solution was 11.2. 100 g solution contained 16 mmol folic acid, disodium salt, 0.1 mmol dihydrofolic acid, sodium salt, and 10 mmol trisodium citrate.

Preparation D

An aqueous solution of folic acid and citric acid was prepared using sodium hydroxide solution. The pH value of the solution was 10.3. 100 g solution contained 16 mmol folic acid, disodium salt, and 12 mmol trisodium citrate.

Preparation E

An aqueous solution of folic acid, dihydrofolic acid and citric acid was prepared using sodium hydroxide solution and calcium hydroxide. The pH value of the solution was 10.4. 100 g solution contained 5 mmol folic acid, calcium salt, 1 mmol dihydrofolic acid, sodium salt, and 7 mmol trisodium citrate.

Preparation F

An aqueous solution of folic acid, dihydrofolic acid and citric acid was prepared using diethanolamine. The pH value of the solution was 9.6. 100 g solution contained 22 mmol folic acid, diethanolamine salt, 2 mmol dihydrofolic acid, diethanolamine salt, and 8,2 mmol citric acid, diethanolamine salt.

Preparation G

An aqueous solution of folic acid, dihydrofolic acid and tartaric acid was prepared using sodium hydroxide solution. The pH value of the solution was 10.4. 100 g solution contained 16 mmol folic acid, disodium salt, 4 mmol dihydro folic acid, sodium salt, and 4 mmol tartaric acid, disodium salt.

Preparation H

An aqueous solution of folic acid and ethylenediaminetetraacetic acid was prepared using sodium hydroxide solution and potassium hydroxide solution. The pH value of the solution was 11. 100 g solution contained 16 mmol folic acid, disodium salt, and 8 mmol ethylenediaminetetraacetic acid, tetrapotassium salt.

Preparation I

An aqueous solution of folic acid and ethylenediaminetetraacetic acid was prepared using sodium hydroxide solution and potassium hydroxide solution. The pH value of the solution was 11. 100 g solution contained 16 mmol folic acid, disodiumsalt, and 16 mmol ethylenediaminetetraacetic acid, tetrapotassium salt.

Preparation J

An aqueous solution of folic acid, dihydrofolic acid and citric acid was prepared using potassium hydroxide solution and calcium hydroxide. The pH value of the solution was 10.8. 100 g solution contained 5 mmol folic acid, calcium salt, 0,2 mmol dihydrofolic acid, potassium salt, and 3 mmol trikalium citrate.

Preparation K

An aqueous solution of folic acid, dihydrofolic acid and tartaric acid and of ethylene glycol was prepared using sodium hydroxide solution. The pH value of the solution was 10.4. 100 g solution contained 16 mmol folic acid, disodium salt, 1 mmol dihydrofolic acid, sodium salt, 4 mmol tartaric acid, disodium salt, and 300 mml ethylene glycol.

Preparation L

An aqueous solution of folic acid, dihydrofolic acid and citric acid was prepared using sodium hydroxide solution and potassium hydroxide solution. The pH value of the solution was 10.4. 100 g solution contained 8 mmol folic acid, disodium salt, 8 mmol dihydrofolic acid, sodium salt, and 5 mmol tripotassium citrate.

Preparation M

An aqueous solution of folic acid, dihydrofolic acid and ethylenediaminetetraacetic acid was prepared using sodium hydroxide solution. The pH value of the solution was 10 4. 100 g solution contained 10 mmol folic acid, disodium salt, 1 mmol dihydrofolic acid, sodium salt, and 6 mmol ethylenediaminetetraacetic acid, tetrasodium salt.

Preparation N

An aqueous solution of folic acid, dihydrofolic acid and ethylenediaminetetraacetic acid was prepared using sodium hydroxide solution. The pH value of the solution was 10.4. 100 g solution contained 10 mmol folic acid, disodium salt, 4 mmol dihydrofolic acid, sodium salt, and 8 mmol ethylenediaminetetraacetic acid, tetrasodium salt.

Preparation O

An aqueous solution of folic acid, dihydrofolic acid and glycolic acid was prepared using sodium hydroxide solution. The pH value of the solution was 10.4. 100 g solution contained 16 mmol folic acid, disodium salt, 1 mmol dihydrofolic acid, sodium salt, and 10 mmol sodium glycolate.

Preparation P

An aqueous solution of folic acid, dihydrofolic acid and succinic acid was prepared using sodium hydroxide solution. The pH value of the solution was 10.4. 100 g solution contained 16 mmol folic acid, disodium salt, 1 mmol dihydrofolic acid, sodium salt, and 10 mmol disodium succinate.

Preparation Q

An aqueous solution of folic acid, dihydrofolic acid and malic acid was prepared using sodium hydroxide solution. The pH value of the solution was 10.4. 100 g solution contained 16 mmol folic acid, disodium salt, 1 mmol dihydrofolic acid, sodium salt, and 10 mmol malic acid, disodium salt.

Preparation R

An aqueous solution of folic acid was prepared using sodium hydroxide solution. The pH value of the solution was 10.4. 100 g solution contained 16 mmol folic acid, disodium salt.

As can be seen from the following Table I, preparations A, C, E, F, G, J, K, L and Q of the invention had an excellent storage stability, in contrast to the other folic acid preparations, which had no stabilizer or a stabilizer, which does not fall under the invention.

TABLE I

| Ex. | Preparation | Storage Time (days) | Stability (%) | Remarks |
|---|---|---|---|---|
| 1 | A | 280 | 92 | invention |
| 2 | B | 280 | 78 | |
| 3 | C | 280 | 95 | invention |
| 4 | D | 280 | 75 | |
| 5 | E | 280 | 91 | invention |
| 6 | F | 200 | 92 | invention |
| 7 | G | 280 | 88 | invention |
| 8 | H | 280 | 62 | |
| 9 | I | 280 | 65 | |
| 10 | J | 260 | 87 | invention |
| 11 | K | 280 | 89 | invention |
| 12 | L | 260 | 96 | invention |
| 13 | M | 200 | 75 | |
| 14 | N | 200 | 76 | |
| 15 | O | 200 | 72 | |
| 16 | P | 200 | 68 | |
| 17 | Q | 200 | 82 | invention |
| 18 | R | 200 | 30 | |

EXAMPLE 19

100 g of the vitamine preparations A and R having the composition given in the above examples were stored 280 days in an open brown glass bottle having a contents of 280 ml at room temperature. At the end of this storage period the measured evaporation losses were made up for by water.

The vitamine preparation was then added to a heavily loaded sample of activated sludge/sewage (BTS=0.8), drawn from a communal sewage treatment plant, in a ratio of 0,26 mg vitamine preparation per 1 sludge/water suspension. The suspension was poisoned with 150 mg/1 phenol and the breathing activity of the poisoned activated sludge was measured in a Warburg apparatus. The results are given in the following Table II.

TABLE II

| Vitamine Preparation | $Y^*_{max}$ value (mg $O_2$/gN, min) | % change over control |
|---|---|---|
| no | 10,4 | — |
| "A" | 18,4 | +77 |
| "R" | 11,6 | +12 |

The activated sludge sample containing the stabilized preparation A according to the invention had a significantly higher degradation rate, as compared to the activated sludge sample containing preparation R, which does not fall under the invention.

EXAMPLE 20

A vitamine preparation was prepared by thoroughly mixing 470 g folic acid dihydrate, calcium salt, 30 g dihydromixing folic acid hydrate, calcium salt, and 500 g citric acid dihydrate. 340 g wet blood meal, containing 200 g water, and 10 g of the vitamine preparation mentioned above were blended at 80° C. and dried on a roll.

The obtained product had a residual humidity of 13% and a folic acid contents, determined microbiologically, of 2.40 percent by weight. After storage over 6 months at 25° C., the microbiologically determined folic acid contents was still 2.15 percent by weight, corresponding to 90% of the value originally measured.

EXAMPLE 21 (COMPARATIVE EXAMPLE)

340 g wet blood meal, containing 200 g water, and 5 g folic acid dihyclate were mixed at 80° C. and dried on a roll.

The obtained product had a residual humidity of 14% and a microbiologically determined folic acid contents of 3.0 percent by weight. After storage over 6 months at 25° C. the microbiologically determined folic acid contents still was 1.9 percent by weight, corresponding to 63% of the value originally measured.

I claim:

1. A stabilized aqueous folic acid preparation comprising a folic acid component selected from the group consisting of folic acid, ammonium, alkali metal, magnesium, calcium, and strontium salts thereof, and mixtures thereof, which has improved stability of its folic acid contents in the presence of oxygen, the said preparation containing as a stabilizer of said folic acid a combination of
   (a) at least one member selected from the group consisting of dihydrofolic acid and ammonium, alkali metal, magnesium, calcium, strontium, and lower alkanolammonium salts thereof, and,
   (b) at least one member selected from the group consisting of citric acid, tartaric acid and malic acid and ammonium, alkali metal, magnesium, calcium, strontium and lower alkanolammonium salts thereof.

2. The preparation of claim 1, wherein the alkanolammonium salt is a salt of the organic acid with an alkanolamine of the formula

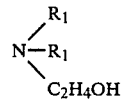

wherein each $R_1$ individually is a member selected from the group consisting of hydrogen, hydroxyethyl and hydroxypropyl.

3. The preparation of claim 1 containing 0.001 to 0.1 mol of stabilized component (a) and 0.05 to 2.5 mol of stabilizer component (b) per mol of the folic acid component.

4. The preparation of claim 3, which contains 0.01 to 0.1 mol of stabilizer component (a) per mol of the folic acid component.

5. The preparation of claim 3, wherein the alkanolammonium salt is a salt of the organic acid with an alkanolamine of the formula

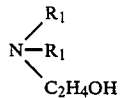

wherein each $R_1$ individually is a member selected from the group consisting of hydrogen, hydroxyethyl and hydroxypropyl.

* * * * *